(12) United States Patent
Novitsky et al.

(10) Patent No.: US 6,171,807 B1
(45) Date of Patent: *Jan. 9, 2001

(54) DETECTION AND QUANTITATION OF ENDOTOXIN BY FLUORESCENCE POLARIZATION

(75) Inventors: Thomas J. Novitsky; Richard J. Ridge, both of Falmouth; Jack L. Sloyer, Cotuit, all of MA (US)

(73) Assignee: Associates of Cape Cod, Inc., Falmouth, MA (US)

(*) Notice: Under 35 U.S.C. 154(b), the term of this patent shall be extended for 0 days.

(21) Appl. No.: 08/967,038

(22) Filed: Nov. 10, 1997

Related U.S. Application Data

(60) Provisional application No. 60/030,594, filed on Nov. 13, 1996.

(51) Int. Cl.[7] .................. G01N 33/53; G01N 33/533; G01N 33/532; G01N 33/531
(52) U.S. Cl. .................. 435/7.8; 435/7.2; 435/7.1; 436/546; 436/544; 436/543; 530/350
(58) Field of Search .................. 435/7.1, 7.8, 7.2, 435/7.32; 530/350, 345; 436/543, 544, 546, 800; 424/184.1, 185.1, 190.1; 514/936

(56) References Cited

U.S. PATENT DOCUMENTS

| | | | |
|---|---|---|---|
| 4,894,348 | * 1/1990 | Robert et al. | 436/546 |
| 4,902,630 | 2/1990 | Bennett et al. | 436/546 |
| 4,906,567 | * 3/1990 | Connelly | 435/7 |
| 5,594,113 | * 1/1997 | Wainwright et al. | 530/395 |
| 5,610,075 | 3/1997 | Stahl-Rees | 436/501 |
| 5,614,369 | * 3/1997 | Wainwright | 435/7.8 |
| 5,770,694 | * 6/1998 | Scott et al. | 530/350 |

FOREIGN PATENT DOCUMENTS

| | | |
|---|---|---|
| WO 92/20715 | 11/1992 | (WO). |
| WO 97/23235 | 7/1997 | (WO). |

OTHER PUBLICATIONS

Khemlani et al. J. cell Biology 115 (3 Part 2): 362 A (1991).*
Yoshida et al. Nippon Shokakibyo Gakkai Zasshi 82(B): 1894–1900, 1985.*

Grogg, Abbot Imx. In: The Immunoassay Handbook, David Wild (ed.) 1994, pp. 137–148.*

Hoess, A. et al., "Cyclic Peptides Derived from Limulus Anti–LPS Factor Bind Endotoxin with High Affinity," *Vaccines96: Molecular Approaches to the Control of Infectious Diseases*, Brown, F. et al., Eds., Cold Spring Harbor Laboratory Press, Cold Spring Harbor, NY; pp. 121–125 (May 1996).

Iwanaga, S. et al., "Molecular Mechanism of Hemolymph Clotting System in Limulus," *Thrombosis Res.* 68(1):1–32 (1992).

Kloczewiak, M. et al., "Synthetic Peptides that Mimic the Binding Site of Horseshoe Crab Antilipopolysaccharide Factor," *J. Infect. Dis.* 170(6): 1490–1497 (1994).

Roche, A.–C. et al., "Interaction between Vesicles Containing Gangliosides and Limulin (*Limulus polyphemus* Lectin)," *FEBS Lett.* 93(1):91–96 (1978).

Yoshida, K. and Ozawa, A., "Quantitative Assay of Endotoxin Using Fluorescent Probe," *Nippon Shokakibyo Gakkai Zasshi* 82(8): 1894–1900 (1985), and English language abstract, p. 1900.

International Search Report for Application No. PCT/US97/20556 (mailed Apr. 1998).

* cited by examiner

*Primary Examiner*—Nita Minnifield
*Assistant Examiner*—S. Devi
(74) *Attorney, Agent, or Firm*—Sterne, Kessler, Goldstein & Fox P.L.L.C.

(57) ABSTRACT

Fluorescently labeled ENP as well as methods of preparation are disclosed. Also disclosed is a method of detecting endotoxin in a liquid sample suspected of containing endotoxin, comprising admixing said liquid sample with fluorescently labeled ENP for a time sufficient to form a complex between the labeled ENP and the endotoxin, and performing fluorescence polarization experiment on the sample, wherein a change in the fluorescence polarization indicates the presence of endotoxin.

13 Claims, 4 Drawing Sheets

REACTION SPECIFICITY- REVERSAL BY UNLABELED R-ENP AND N-ENP

|  | mP | % CHANGE IN mP |
|---|---|---|
| TRACER | 186 | |
| LPS | 312 | 68% INCREASE |
| UNLABELED R-ENP | 218 | 30% DECREASE |
| UNLABELED N-ENP | 274 | 12% DECREASE |

FIG.4

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 101 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:1:

```
Asp Gly Ile Trp Thr Gln Leu Ile Phe Thr Leu Val Asn Asn Leu Ala
1               5                   10                  15
```

```
Thr Leu Trp Gln Ser Gly Asp Phe Gln Phe Leu Asp His Glu Cys His
        20                  25                  30

Tyr Arg Ile Lys Pro Thr Phe Arg Arg Leu Lys Trp Lys Tyr Lys Gly
            35                  40                  45

Lys Phe Trp Cys Pro Ser Trp Thr Ser Ile Thr Gly Arg Ala Thr Lys
50                  55                  60

Ser Ser Arg Ser Gly Ala Val Glu His Ser Val Arg Asn Phe Val Gly
65                  70                  75                  80

Gln Ala Gly Ser Ser Gly Leu Ile Thr Gln Arg Gln Ala Glu Gln Phe
                85                  90                  95

Ile Ser Gln Tyr Asn
            100
```

(2) INFORMATION FOR SEQ ID NO:2:

(i) SEQUENCE CHARACTERISTICS:
        (A) LENGTH: 331 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..315

(xi) SEQUENCE DESCRIPTION: SEQ ID NO:2:

```
GAG GCT GAA GCT GAC GGT ATC TGG ACC CAA TTG ATT TTC ACT TTG GTT     48
Glu Ala Glu Ala Asp Gly Ile Trp Thr Gln Leu Ile Phe Thr Leu Val
 1               5                  10                  15

AAC ATT TTG GCC ACC TTA TGG CAG TCC GGT GAT TTT CAA TTC TTG GAC     96
Asn Ile Leu Ala Thr Leu Trp Gln Ser Gly Asp Phe Gln Phe Leu Asp
                20                  25                  30

CAC GAA TGT CAC TAC AGA ATC AAG CCA ACT TTC AGA AGA TTG AAG TGG    144
His Glu Cys His Tyr Arg Ile Lys Pro Thr Phe Arg Arg Leu Lys Trp
            35                  40                  45

AAA TAT AAG GGT AAA TTT TGG TGT CCA TCT TGG ACC TCT ATT ACT GGT    192
Lys Tyr Lys Gly Lys Phe Trp Cys Pro Ser Trp Thr Ser Ile Thr Gly
 50                  55                  60

AGA GCT ACC AAG TCT TCT AGA TCC GGT GCT GTC GAA CAC TCT GTT AGA    240
Arg Ala Thr Lys Ser Ser Arg Ser Gly Ala Val Glu His Ser Val Arg
65                  70                  75                  80

AAC TTC GTC GGT CCA GCT AAG TCT TCC GGT TTG ATC ACT GAA AGA CAA    288
Asn Phe Val Gly Pro Ala Lys Ser Ser Gly Leu Ile Thr Glu Arg Gln
                85                  90                  95

GCT GAA CAA TTC ATT TCT CAA TAC AAC TGATAAGCTT GAATTC              331
Ala Glu Gln Phe Ile Ser Gln Tyr Asn
            100                 105
```

(2) INFORMATION FOR SEQ ID NO:3:

(i) SEQUENCE CHARACTERISTICS:
        (A) LENGTH: 105 amino acids
        (B) TYPE: amino acid
        (D) TOPOLOGY: linear (ii) MOLECULE TYPE: protein (xi) SEQUENCE DESCRIPTION: SEQ ID NO:3:

```
Glu Ala Glu Ala Asp Gly Ile Trp Thr Gln Leu Ile Phe Thr Leu Val
 1               5                  10                  15

Asn Ile Leu Ala Thr Leu Trp Gln Ser Gly Asp Phe Gln Phe Leu Asp
```

-continued

|  |  |  |  | 20 |  |  |  | 25 |  |  |  | 30 |  |  |
|---|---|---|---|---|---|---|---|---|---|---|---|---|---|---|
| His | Glu | Cys | His | Tyr | Arg | Ile | Lys | Pro | Thr | Phe | Arg | Arg | Leu | Lys | Trp |
|  |  |  | 35 |  |  |  |  | 40 |  |  |  |  | 45 |  |  |
| Lys | Tyr | Lys | Gly | Lys | Phe | Trp | Cys | Pro | Ser | Trp | Thr | Ser | Ile | Thr | Gly |
|  | 50 |  |  |  |  | 55 |  |  |  |  | 60 |  |  |  |  |
| Arg | Ala | Thr | Lys | Ser | Ser | Arg | Ser | Gly | Ala | Val | Glu | His | Ser | Val | Arg |
| 65 |  |  |  |  | 70 |  |  |  |  | 75 |  |  |  |  | 80 |
| Asn | Phe | Val | Gly | Pro | Ala | Lys | Ser | Ser | Gly | Leu | Ile | Thr | Glu | Arg | Gln |
|  |  |  |  | 85 |  |  |  |  | 90 |  |  |  |  | 95 |  |
| Ala | Glu | Gln | Phe | Ile | Ser | Gln | Tyr | Asn |  |  |  |  |  |  |  |
|  |  |  | 100 |  |  |  |  | 105 |  |  |  |  |  |  |  |

DETECTION AND QUANTITATION OF ENDOTOXIN BY FLUORESCENCE POLARIZATION

This application claims benefit of provisional application 60/030,594 filed Nov. 13, 1996.

BACKGROUND OF THE INVENTION

1. Field of the Invention

The present invention is in the field of fluorescence polarization assays for endotoxin.

2. Related Art

Fluorescence polarization was first described in 1926 (Perrin, *J. Phys. Rad.* 1:390–401 (1926)) and has been a powerful tool in the study of molecular interactions. When fluorescent molecules are excited with plane polarized light, they emit light in the same polarized plane, provided that the molecule remains stationary throughout the excited state (4 nanoseconds in the case of fluorescein). However, if the excited molecule rotates or tumbles out of the plane of polarized light during the excited state, then light is emitted in a different plane from that of the initial excitation. If vertically polarized light is used to excite the fluorophore, the emission light intensity can be monitored in both the original vertical plane and also the horizontal plane. The degree to which the emission intensity moves from the vertical to horizontal plane is related to the mobility of the fluorescently labeled molecule. If fluorescently labeled molecules are very large, they move very little during the excited state interval, and the emitted light remains highly polarized with respect to the excitation plane. If fluorescently labeled molecules are small, they rotate or tumble faster, and the resulting emitted light is depolarized relative to the excitation plane. "Introduction to Fluorescence Polarization," Pan Vera Corp., Madison, Wis., Jun. 17, 1996.

Fluorescence polarization (FP) is defined as:

$$FP = \frac{Int\|-Int\bot}{Int\|+Int\bot}$$

Where Int(parallel) is the intensity of the emission light parallel to the excitation light plane and Int(perpendicular) is the intensity of the emission light perpendicular to the excitation light plane. FP, being a ratio of light intensities, is a dimensionless number and has a maximum value of 0.5 for fluorescein. The Beacon System expresses polarization in millipolarization units (1 Polarization Unit=1000 mP Units). "Introduction to Fluorescence Polarization," Pan Vera Corp., Madison, Wis., Jun. 17, 1996.

Fluorescence anisotropy (A) is another term commonly used to describe this phenomenon. Polarization and anisotropy are related in the following way.

$$A = \frac{Int\|-Int\bot}{Int\|+2Int\bot} \text{ and } A = \frac{2P}{3-P}$$

As discussed above, polarization is related to the speed at which a fluorescently labeled molecule rotates. The Perrin equation can be used to show that polarization is directly proportional to the correlation time, the time that it takes a molecule to rotate through an angle of approximately 68.5°. The correlation time is sometimes referred to as the rotational relaxation time or the rotational correlation time. Correlation time is related to viscosity (n), absolute temperature (T), molecular volume (V), and the gas constant (R) by the following equation.

$$\text{Correlation Time} = \frac{3\eta V}{RT}$$

It follows then, that if viscosity and temperature are held constant, correlation time, and therefore polarization, are directly related to the molecular volume. Changes in molecular volume may be due to molecular binding, dissociation, synthesis, degradation, or conformational changes of the fluorescently labeled molecule.

Light from a monochromatic source passes through a vertical polarizing filter to excite fluorescent molecules in the sample tube. Only those molecules that are orientated in the vertically polarized plane absorb light, become excited, and subsequently emit light. The emission light intensity is measured both parallel and perpendicular to the exciting light. The fraction of the original incident, vertical light intensity that is emitted in the horizontal plane is a measure of the amount of rotation the fluorescently labeled molecule has undergone during the excited state, and therefore is a measure of its relative size. See, "Introduction to Fluorescence Polarization," Pan Vera Corp., Madison, Wis., Jun. 17, 1996. Other publications describing the FP technique include G. Weber, *Adv. Protein Chem.* 8:415–59 (1953); W. B. Dandliker and G. A. Feigen, *Biochem. Biophys. Res. Commun.* 5:299–304 (1961); W. B. Dandliker et al., *Immunochemistry* 10:219–27 (1973); and M. E. Jolley, *J. Anal. Toxicol.* 5:236–240 (1981). "Chapter 4—Introduction to Fluorescence Polarization," the FPM-1™ Operators Manual, pp. 9–10, Jolley Consulting and Research, Inc. Grayslake, Ill.

One of the most widely used fluorescence polarization applications is the competitive immunoassay used for the detection of therapeutic and illicit drugs. A small, fluorescently-labeled drug, when excited with plane polarized light, emits light that is depolarized because the fluorophore is not constrained from rotating during the excitation state. When the labeled drug is added to a serum-antibody mixture, it competes with the unlabeled drug in the sample for binding to the antibody. The lower the concentration of unlabeled drug in the sample, the greater amount of labeled drug that will bind to the antibody. Once bound to antibody, the labeled drug rotates and tumbles more slowly. Light emitted by the fluorescently labeled drug/antibody complex will be more polarized, and the fluorescence polarization value of the sample will be higher. By constructing a standard curve of serum samples with known drug concentrations versus polarization value, the concentration of drug in a patient sample can be easily determined. "Introduction to Fluorescence Polarization," Pan Vera Corp., Madison, Wis., Jun. 17, 1996; Perrin, *J. Phys. Rad.* 1:390–401 (1926).

FP measurements can be made using Pan Vera's Beacon® Fluorescence Polarization system, which can detect as little as 10 femtomoles/ml of fluorescently labeled sample. Measurements are made on samples directly in solution and, as a result, the need for any separation or filtration of bound from unbound elements is eliminated.

Most buffers and salts are contaminated with fluorescence and give background readings that are too high for measurements in the pM or even nM range. Pan Vera offers a line of low fluorescence buffers and reagents that allows one to measure fluorescence polarization values to low pM concentrations.

The abridged version of the Beacon® Fluorescence Polarization Applications Guide provides examples of a wide range of molecular binding (and enzymatic degradation) experiments performed on the Beacon FP system.

The Limulus Amoebocyte Assay (LAL) is an assay for endotoxin or bacteria which have endotoxin on their cell surfaces.

Another assay for endotoxin employs the endotoxin binding and neutralizing protein (ENP). ENP may be isolated from the horseshoe crab (Seq ID NO: 1) or produced recombinantly. When produced recombinantly in a yeast host, a modified ENP is obtained which contains GluAla-GluAla at the N-terminus (SEQ ID NO:3). ENP can be used to detect endotoxin in samples in a qualitative and quantitative fashion, as well as for treating endotoxemia in vivo. See International Application Publication No. WO92/20715 and U.S. application Ser. No. 08/264,244, filed Jun. 22, 1994.

SUMMARY OF THE INVENTION

The invention relates to fluorescently labeled ENP.

The invention also relates to a method of preparing fluorescently labeled ENP, comprising combining in a solution ENP and a fluorescence labeling reagent, and isolating the fluorescently labeled ENP from the solution.

In particular, the invention relates to a method of preparing fluorescently labeled ENP, comprising combining in an aqueous citrate buffer solution ENP having SEQ ID NO: 3, urea and FS, and isolating the fluorescently labeled ENP from the solution.

The invention also relates to a method of detecting endotoxin in a liquid sample suspected of containing endotoxin, comprising admixing said liquid sample with fluorescently labeled ENP for a time sufficient to form a complex between the labeled ENP and the endotoxin, and performing a fluorescence polarization experiment on said sample, wherein a change in the fluorescence polarization indicates the presence of endotoxin. In this embodiment, the fluorescence polarization experiment comprises (a) inserting a control container containing buffer or water into the fluorescence polarization analyzer;

(b) adding a predetermined amount of a standard solution comprising fluorescently labeled ENP to the control container and measuring the fluorescence polarization to give a baseline measure of fluorescence polarization;

(c) adding to the solution obtained in step (b) a series of known concentrations of LPS and recording the changes in fluorescence polarization; and (d) adding to the solution obtained in step (b) or step (c) the sample suspected of containing endotoxin and recording the change of fluorescence polarization;

whereby the change in fluorescence polarization recorded in step (d) indicates the presence of endotoxin.

The invention also relates to a method of quantifying endotoxin in a liquid sample suspected of containing endotoxin, comprising admixing said liquid sample with fluorescently labeled ENP for a time sufficient to form a complex between the labeled ENP and the endotoxin, and performing a fluorescence polarization experiment on said sample, wherein the relative change in the fluorescence polarization is a measure of the quantity of endotoxin in said sample. In this embodiment, the fluorescence polarization experiment comprises (a) inserting a control container containing buffer or water into the fluorescence polarization analyzer;

(b) adding a predetermined amount of a standard solution comprising fluorescently labeled ENP to the control container and measuring the fluorescence polarization to give a baseline measure of fluorescence polarization;

(c) adding to the solution obtained in step (b) a series of known concentrations of LPS, recording the changes in fluorescence polarization, and plotting the changes to give a standard curve; and (d) adding to the solution obtained in step (b) or step (c) the sample suspected of containing endotoxin and recording the change of fluorescence polarization;

whereby the relative change in fluorescence polarization recorded in step (d) is a measure of the concentration of endotoxin in said sample.

The invention also relates to a method of detecting endotoxin in a liquid sample suspected of containing endotoxin, comprising (a) admixing a defined concentration of ENP with a defined concentration of fluorescently labeled LPS for a time sufficient to form a complex between the labeled LPS and the ENP, (b) performing a fluorescence polarization (FP) experiment on the admixture obtained according to step (a) to give a first FP value, (c) admixing a sample suspected of containing endotoxin with the admixture obtained in step (a), and (d) performing a FP experiment on the admixture obtained in step (c) to give a second FP value, wherein a change in the second FP value with respect to the first FP value indicates the presence of endotoxin.

The invention also relates to a method of quantifying endotoxin in a liquid sample suspected of containing endotoxin, comprising (a) admixing a defined concentration of ENP with a defined concentration of fluorescently labeled LPS for a time sufficient to form a complex between the labeled LPS and the ENP, (b) performing a fluorescence polarization (FP) experiment on the admixture obtained according to step (a) to give a first FP value, (c) admixing a sample suspected of containing endotoxin to the admixture obtained in step (a), and (d) performing a FP experiment on the admixture obtained in step (c) to give a second FP value, wherein the relative change in the second FP value with respect to the first FP value is a measure of the quantity of endotoxin in said sample.

BRIEF DESCRIPTION OF THE FIGURES

FIG. 4 depicts a table showing the reaction specificity—reversal by unlabeled R-ENP and N-ENP.

DETAILED DESCRIPTION OF THE PREFERRED EMBODIMENTS

Figure 1:
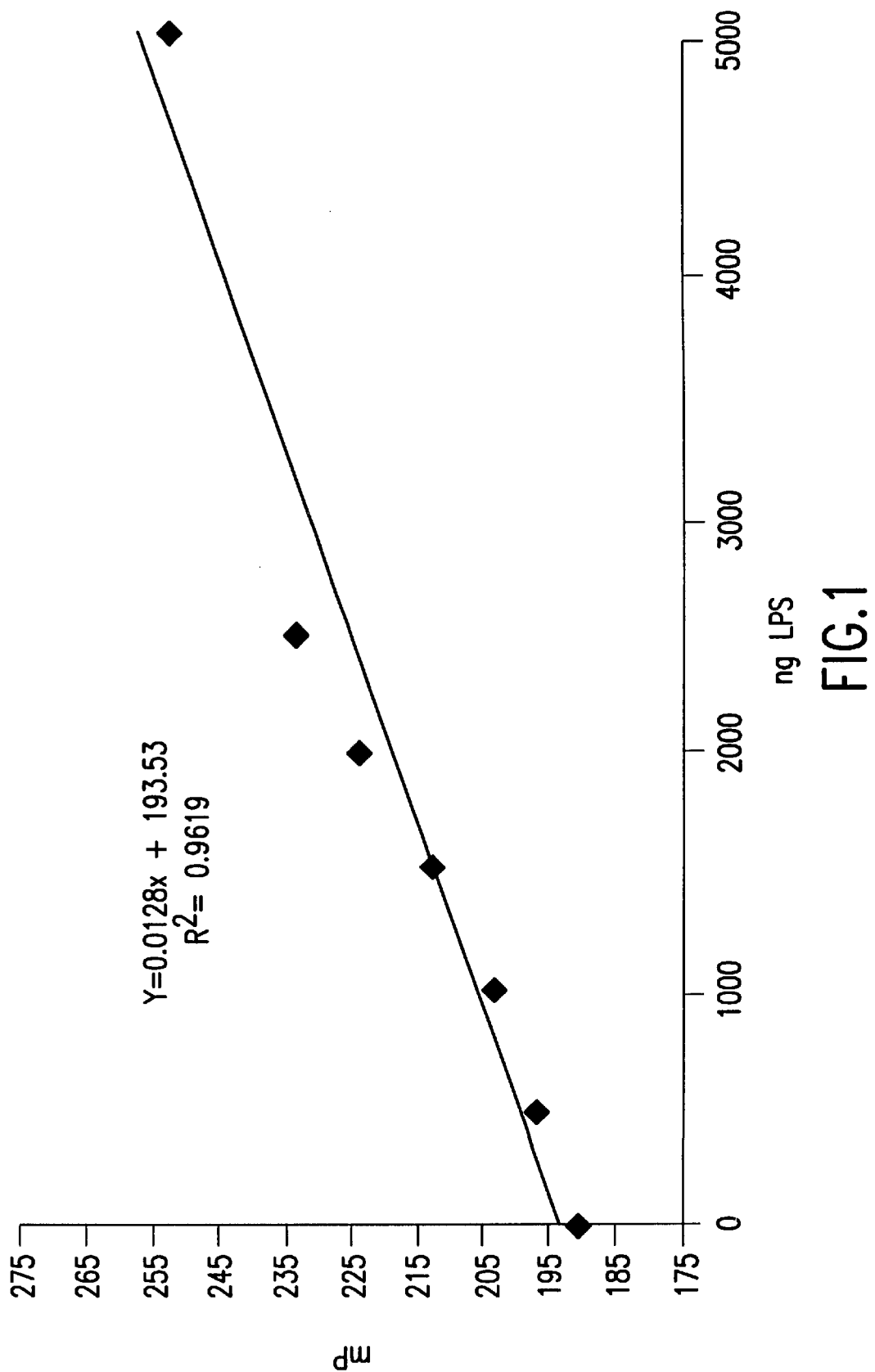
FIG. 1 depicts a graph showing a standard curve obtained with fluorescein labeled recombinant ENP (SEQ ID NO:3), prepared with urea, against various concentrations of endotoxin (LPS) in phosphate buffer (pH 6.6).
Figure 2:
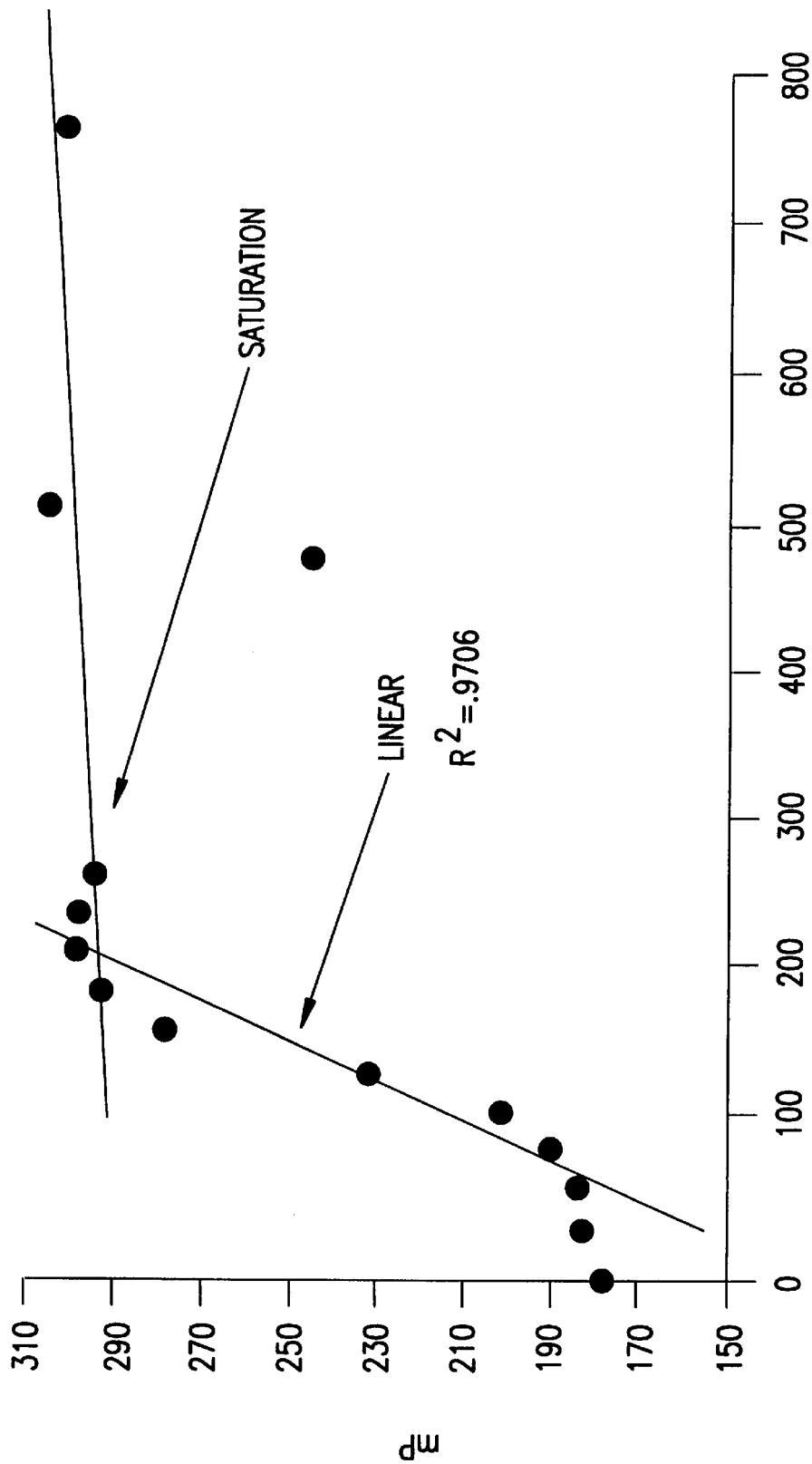
FIG. 2 depicts a graph showing a standard curve obtained with fluorescein labeled recombinant ENP showing a linear portion and saturation of LPS binding when tested in pyrogen free water "buffer".
Figure 3:
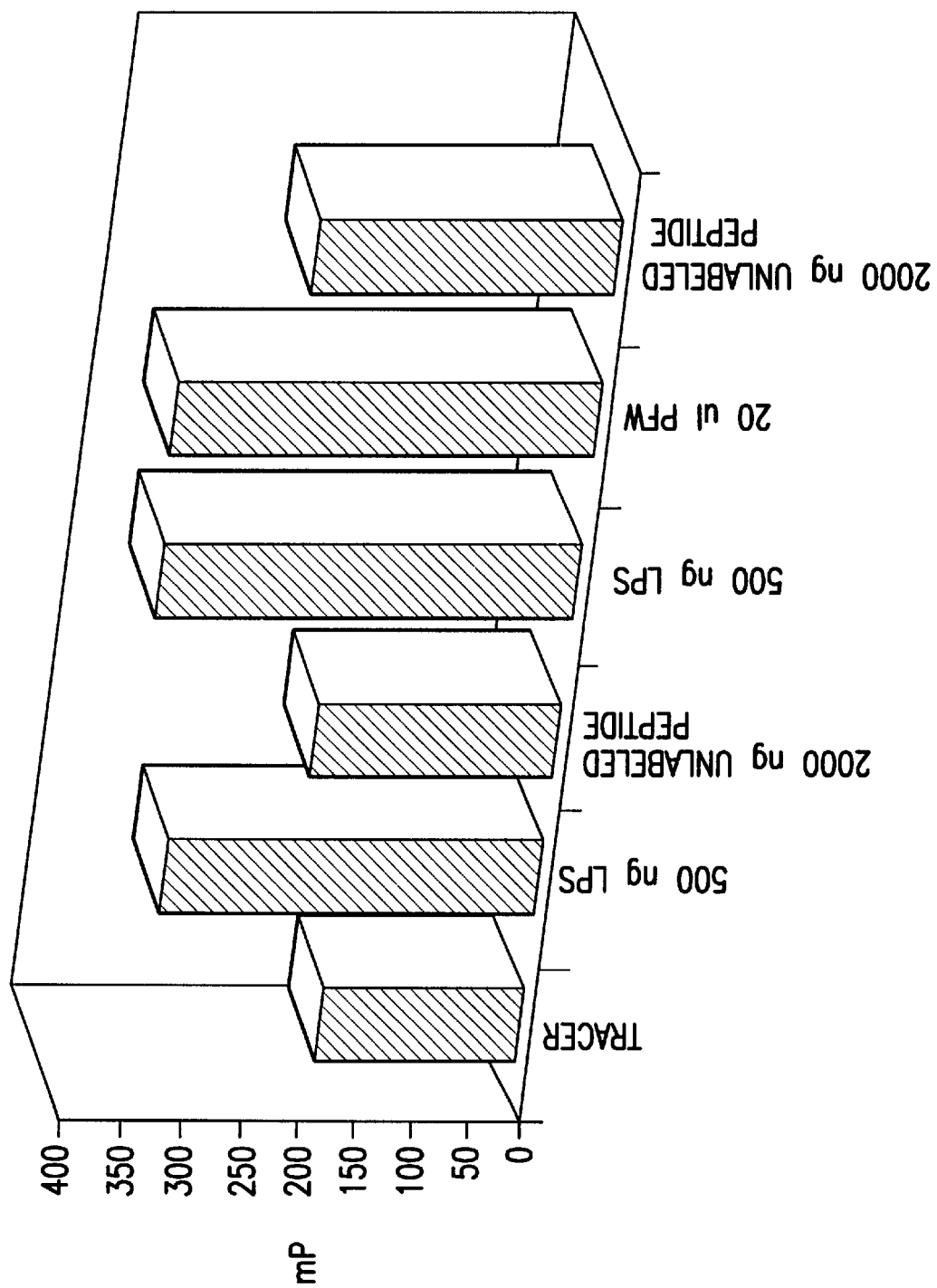
FIG. 3 depicts a bar graph showing the reaction specificity of the assay with fluorescein labeled recombinant ENP. The results show that the addition of LPS increases mP. The addition of unlabeled peptide reduces mP. The addition of a second aliquot of LPS again raises mP. The addition of water (pyrogen free water, PFW) causes no change, while a second addition of unlabeled peptide causes a second reduction in mP.

There are several abbreviations used herein as listed below:
ENP=Endotoxin Neutralizing Protein
R-ENP=Recombinant ENP, N-ENP=Natural ENP
FP=Fluorescence Polarization
LPS=Lipopolysaccharide, used interchangeably for Endotoxin and for Pyrogen
PFW=Pyrogen Free Water
FITC=Fluorescein-isothiocyanate, a fluorophore
pH=a measure of acidity, the lower the pH the more acidic
HPLC=High Performance Liquid Chromatography
RPHPLC=Reverse Phase HPLC
FS=fluorescein N-hydroxysuccinimide ester
EU=Endotoxin Unit, a measure of LPS concentration
DMSO=Dimethyl sulfoxide
TFA=Trifluoroacetic acid
Limulus Amoebocyte Assay=LAL LAL has been the assay of choice for the detection and quantitation of endotoxin. Several aspects about the LAL test have prompted researchers to look for alternative tests which have the potential for eliminating or minimizing some of the difficulties encountered in using LAL. This invention is directed to the use of FP in combination with fluorescently-labeled ENP or LPS to detect bacterial endotoxin. In addition, the invention provides procedures and reagents for labeling the ENP as well as buffers for using the assay.

The basis for FP lay with the fact that molecular rotation is altered relative to the size of the molecule. Therefore by using specific reagents which have a fluorophore attached to them and whose size can only be altered by specific molecules, one can measure the rotation and fluorescence polarization with a special fluorometer and relate the rotation to the concentration of the molecule responsible for changing the molecular size of the labeled reagent. It is expected that the FP assay will be a direct one, that is, the measurement of the slowing of the rotation, i.e., an increase in polarization, is directly proportional to the concentration of the rotation altering molecule.

It is expected that the FP assay will replace the LAL assay in the measurement of endotoxin, both soluble and that which is bound to surfaces including that which is associated with Gram-negative bacteria. In addition to measuring endotoxin, the method of the invention may be used to measure molecules specific for Gram positive bacteria and fungi, as well as biocides and antibiotics.

The practice of the first method of detecting endotoxin in a liquid sample suspected of containing endotoxin involves admixing the liquid sample with fluorescently labeled ENP for a time sufficient to form a complex between the labeled ENP and the endotoxin, and performing fluorescence polarization experiment on said sample, wherein a change in the fluorescence polarization indicates the presence of endotoxin. Preferably, the concentration of fluorescently labeled ENP is about 10 picograms to 100 nanograms, more preferably about 150 picograms. The time sufficient is generally instantaneous, but no more than about 2 min. The temperature may be about 20 to 30° C. Preferably, the temperature is held constant at about 25° C.

In this embodiment, the fluorescence polarization experiment comprises
    (a) inserting a control container containing buffer or water into the fluorescence polarization analyzer;
    (b) adding a predetermined amount of a standard solution comprising fluorescently labeled ENP to the control container and measuring the fluorescence polarization to give a baseline measure of fluorescence polarization;
    (c) adding to the solution obtained in step (b) a series of known concentrations of LPS and recording the changes in fluorescence polarization; and
    (d) adding to the solution obtained in step (c) the sample suspected of containing endotoxin and recording the change of fluorescence polarization;
    whereby the change in fluorescence polarization recorded in step (d) indicates the presence of endotoxin.

The known concentrations of LPS that may be used include, for example, 10 and 100 picograms; 1, 10, and 100 nanograms; and 1 and 10 micrograms.

In the first method of quantitating endotoxin in a liquid sample suspected of containing endotoxin, the invention involves admixing said liquid sample with fluorescently labeled ENP for a time sufficient to form a complex between the labeled ENP and the endotoxin, and performing fluorescence polarization experiment on said sample, wherein the relative change in the fluorescence polarization is a measure of the quantity of endotoxin in said sample. The same parameters of concentration, time and temperature as for the method of quantitating endotoxin also apply to the method of quantitating endotoxin.

In this embodiment, the fluorescence polarization experiment comprises
    (a) inserting a control container containing buffer or water into the fluorescence polarization analyzer;
    (b) adding a predetermined amount of a standard solution comprising fluorescently labeled ENP to the control container and measuring the fluorescence polarization of give a baseline measure of fluorescence polarization;
    (c) adding to the solution obtained in step (b) a series of known concentrations of LPS, recording the changes in fluorescence polarization, and plotting the changes to give a standard curve; and
    (d) adding to the solution obtained in step (c) the sample suspected of containing endotoxin and recording the change of fluorescence polarization;
    whereby the change in fluorescence polarization recorded in step (d) is a measure of the concentration of endotoxin in said sample.

The second method of detecting endotoxin in a liquid sample suspected of containing endotoxin involves:
    (a) admixing a defined concentration of ENP with a defined concentration of fluorescently labeled LPS for a time sufficient to form a complex between the labeled LPS and the ENP,
    (b) performing a fluorescence polarization (FP) experiment on the admixture obtained according to step (a) to give a first FP value,
    (c) admixing a sample suspected of containing endotoxin with the admixture obtained in step (a), and
    (d) performing a FP experiment on the admixture obtained in step (c) to give a second FP value,
wherein a change in the second FP value with respect to the first FP value indicates the presence of endotoxin.

The second method of quantifying endotoxin in a liquid sample suspected of containing endotoxin involves
    (a) admixing a defined concentration of ENP with a defined concentration of fluorescently labeled LPS for a time sufficient to form a complex between the labeled LPS and the ENP,
    (b) performing a fluorescence polarization (FP) experiment on the admixture obtained according to step (a) to give a first FP value,
    (c) admixing a sample suspected of containing endotoxin to the admixture obtained in step (a), and (d) performing a FP experiment on the admixture obtained in step (c) to give a second FP value,
wherein the relative change in the second FP value with respect to the first FP value is a measure of the quantity of endotoxin in said sample.

The defined concentration of ENP may range from about 10 picograms to 100 nanograms per ml, preferably about 150 picograms per ml. The defined concentration of fluorescently labeled LPS is generally equimolar to the concentration of ENP.

The term "ENP" according to the present invention includes both the protein isolated from the horseshoe crab (SEQ ID NO: 1) as well as the recombinantly produced protein having GluAlaGluAla at the N-terminus thereof (SEQ ID NO: 3) and fragments thereof so long as they are capable of binding LPS when fluorescently labeled. Methods for preparing either form of ENP are disclosed in International Application Publication No. WO92/20715 and U.S. application Ser. No. 08/264,244. See also WO97/23235. Preferably, the ENP has SEQ ID NO: 3. The DNA from which ENP having SEQ ID NO: 3 can be expressed has SEQ ID NO: 2. Of course, the ENP may also be prepared by well known methods of solid phase synthesis. Allelic variations of ENP are known in the art and can also be used in the practice of the invention. Further, fragments of ENP which bind LPS can be used. See Kloczewiak, M., et al., *J. Infect. Dis.* 170:1490–1497 (1994) (who disclose synthetic peptides that mimic the binding site of the horseshoe crab antilipopolysaccharide factor); Hoess, A., et al., *J. Vaccines* 96, Cold Spring Harbor Laboratory Press; Hoess, A., et al., *EMBO J.* 12:3351–3356 (1993); and Iwanaga, S., et al., *Throm. Res* 68:1–32 (1992).

The fluorescent labeled ENP may be prepared as described herein. For example, the ENP may be reacted in an aqueous solution with a fluorescence labeling reagent such as fluorescein-isothiocyanate (FITC), fluorescein N-hydroxysuccinimide ester (FS), BODIPY® (4,4-difluoro-4-bora 3a,4a-diaza-5-indacene)-FL (which has alkyl groups at the 3, 5 and 7- positions, e.g., BODIPY®FL $C_3$-SE (D-2184) which is 4,4-difluoro-5,7-dimethyl-4-bora-3a,4a-diaza-5-indacene-3-proprionic acid, succinimidyl ester), BODIPY®TR-X-SE (D-6116) which is 6-(((4-(4,4-difluoro-5-(2-thienyl)-4-bora-3a,4a-diaza-5-indacene-3-yl)phenoxy)acetyl)amino)hexanoic acid, succinimidyl ester, 4-acetamido-4'-isocyanatostilbene 2,2'-disulfonic acid, 7-amino-4-methylcoumarin, 7-amino-4-trimethylcoumarin, N-(4-anilino-1-naphthyl)maleimide, dansyl chloride, 4',6-diamidino-2-phenylindole, 5-(4,6-dichlorotriazin-2-yl)aminofluorescein, 4,4'-diisothiocyanatostilbene-2,2'-disulfonic acid, eosin isothiocyanate, erythrosin B, fluorescamine, fluorescein-5(6)-carboxamidocaproic acid N-hydroxy succinimide ester, fluorescein 5-isothiocyanante diacetate, 4-methylumbelliferone, o-phthaldialdehyde, QFITC, rhodamine B isothiocyanate, sulforhodamine 101 acid chloride, tetramethyl-rhodamine isothiocyanate, and 2',7'-difluorofluorescein (Oregon Green), most of which are available from Sigma Chemical Company, St. Louis, Mo.

Fluorescently labeled LPS may be prepared by reacting LPS with one of the fluorescence labeling reagents listed above. FS-labeled LPS (FITC-LPS) is commercially available from Sigma Chemical Company.

The materials for use in the assays of the invention are ideally suited for preparation of a kit. Such a kit may comprise a carrier means being compartmentalized to receive in close confinement one or more container means such as vials, tubes and the like. Each of said container means comprises one of the separate elements to be used in the method. For example, one of said container means may comprise fluorescently labeled ENP. A second container means may comprise a buffer solution. A third and fourth container with negative and positive controls, respectively, may be included.

The carrier may also contain, in addition, a plurality of containers each of which comprises different, predetermined and known amounts of endotoxin or Gram negative bacteria, either lysed or whole, and controls. These latter containers can then be used to prepare a standard curve from which can be interpolated the results obtained from the sample containing the unknown amount of endotoxin or Gram negative bacterial contamination.

Alternatively, the kit may comprise a first container means which may comprise fluorescently labeled LPS. A second container means may contain ENP. A third container means may comprise a buffer solution. A fourth and fifth container with negative and positive controls, respectively, may be included.

The kit may comprise a single test ready to use in 12×75 glass test tubes. In this system, a fluorescence polarimeter (FP) single tube reader will be the instrument. The reader will be computer interfaced for ease of data acquisition, storage, and analysis. Since the test is a simple chemical reaction which reaches equilibrium in generally less than one minute, a series of tests can be set up and read later without loss of data. This is not a timed endpoint kinetic reaction. The kit will include vials with the FP reagent in liquid form which should be kept in the dark but probably not refrigerated. A transportable FP unit along with a micropipette with tips may be employed. The user will simply add some microliter amount (between 20 to 100 $\mu$l) into the tube and read the mP which is related to a standard curve. Standard solutions supplied with other FP tests and used to give standard curves appear to be stable for 6 months. The standard curve should be replotted when a different lot of control reagent is used or when a new machine is validated.

Large daily volume users may wish to perform the test in a microplate. In this embodiment, a microplate reader may be employed. The chemistry of the reaction remains the same as for the single test, however, the end user will most likely have to dispense the reagent in the plate wells. FP microplate machines are rather expensive, however, the cost may be offset in time by the labor reduction when compared to the single test tube system.

Potential applications for the FP test for LPS testing, for endotoxin or bacterial contamination, include any one of a number of industrial fluids, e.g. oil-in-water emulsions used as coolants for metal cutting, aluminum and steel rolling, metal forming, rust preventives, metal cleaners, metal heat treating fluids, and similar applications; paints and adhesives; food products and food handling surfaces; waste water and cooling tower water; personal care products; indoor and outdoor air quality; pharmaceutical products; and medical diagnostic products, e.g. blood, urine, CSF, lavages, and other body fluids. Thus, the methods of the invention allow for the detection of soluble endotoxin as well as whole bacterial cells and cell components associated with endotoxin. The samples may be analyzed by various techniques. In the case of liquids, the liquid sample may be tested directly. Surfaces may be swabbed with an endotoxin-free swab using a template placed on the surface. The area of the surface inside the template is swabbed, the swab is placed into one ml of pyrogen free water, vigorously shaken, and the swab removed to give a liquid sample for testing. Air samples suspected of containing endotoxin or bacterial contamination may collected using an impinger connected to a small pump which pulls air into the impinger whose end is submerged in one ml of fluorescently labeled ENP. An aliquot of the sample is then used for testing.

Typical Procedure for Measuring LPS Using Fluorescence Polarization

The FPM-1™ instrument from Jolley Consulting and Research, Inc., Grayslake, Ill., may be used, which is a single tube spectrofluorometric reader with a printout and a computer interface.

A working standard of fluorescently labeled ENP is prepared so that a solution with a relatively low mP and sufficiently high intensity results. Using FS labeled R-ENP prepared according to the procedure described herein, 100 μl of FS-R-ENP labeled ENP is added to 900 μl of pyrogen free water. This is the working standard for use in the following test:

Direct Assay

1. FPM-1 is turned on. Wait 5 minutes for bulb to warm up.

2. Insert a control tube into the FPM-1 containing only 2 ml of buffer (in this case pyrogen free water).

3. Add 20 μl of working standard to the control and remeasure. This is now the baseline mP from which subsequent measures will be evaluated. Ideally the mP should be less than 200 and the intensity above 100,000.

4. To the tube in step #3 add μl quantities of LPS and record changes in mP as a function of the concentration of LPS or other additive under study.

Indirect Assay

1. FPM-1 is turned on. Wait 5 minutes for bulb to warm up.

2. Insert a control tube into the FPM-1 containing only 2 ml of buffer (in this case pyrogen free water).

3. Add 20 μl of working standard to the control and remeasure. This is now the baseline mP from which subsequent measures will be evaluated. Ideally the mP should be less than 200 and the intensity above 100,000.

4. To the tube in step #3 add known concentrations of LPS and record changes in mP.

6. Add μl quantity of sample containing unknown concentration of ENP. The resultant change in mP is proportional to the concentration of the unlabeled ENP.

As shown in the following table, the viscosity of water is dependent on temperature. Since viscosity can affect the FP result, temperature control is important.

TABLE 1

The dependence of the viscosity of water on temperature

| Temp (° C.) | Viscosity (cp) |
|---|---|
| 0 | 1.793 |
| 10 | 1.307 |
| 20 | 1.002 |
| 30 | 0.798 |
| 40 | 0.653 |
| 50 | 0.547 |
| 60 | 0.466 |
| 70 | 0.404 |
| 80 | 0.354 |
| 90 | 0.314 |
| 100 | 0.282 |

The following examples further describe the materials and methods used in carrying out the invention. The examples are not intended to limit the invention in any manner.

EXAMPLE 1

Preparation of Fluorescently Labeled ENP

To a solution of rENP (SEQ ID NO: 3) in 0.1 M sodium citrate, 6 M urea (ultrapure), pH 6 (1 mg/ml, 1 ml) is added a freshly prepared solution of fluorescein N-hydroxysuccinimide ester (FS) (Pan Vera) in DMSO (5 mg/ml, 10 mmolar, 50 μl). The resulting yellow solution is mixed well, centrifuged at 5000 rpm for 2 min, then incubated in a heating block or water bath set at 37° C. for 1 h in the dark. The solution is then mixed with quenching buffer (1 M Tris HCl, pH 8, 100 μl), centrifuged again and kept at room temperature in the dark for 30–60 min.

The final solution is then applied to a PD10 gel filtration column (Pharmacia, freshly washed with appropriate buffer) to separate the product from hydrolyzed labeling reagent. For the above example the column is washed with 0.1 M sodium citrate, pH 6 (25 ml), followed by the same buffer containing 6 M Urea (5 ml). The product is eluted in the latter in a volume of 1.2–1.6 ml, after collection of two fractions of 1.2 ml each, and stored at 4° C. in the dark.

The labeled protein is then isolated from the unreacted (unlabeled) protein. This may be accomplished by reverse-phase high pressure liquid chromatography (RPHPLC), utilizing a C4, 300 Å, 5μ column and 0.1% TFA in water and 0.095% TFA in acetonitrile as solvents. Other methods, such as ion-exchange and affinity chromatography, could also be used.

Results

ENP Labeling Reactions

Experiments #1–13, see Table 1. These experiments used the FITC label because it is the least expensive available and the labeling procedure for many proteins has been well documented. Variables included buffer composition, pH, and molar equivalents of FITC, all of which were studied in an attempt to maximize the labeling of ENP. None of these experiments produced a highly labeled ENP which had superior reactivity with LPS, however, there was sufficient suggestion that the reaction would work if a more highly labeled and directed label procedure could be developed.

Several principles had to be considered in further developing a labeling procedure. First, ENP became increasingly insoluble as pH rose above about 7. Simultaneously, the reaction of FITC with amino groups became less specific but more reactive with amino groups at higher pH, and lastly, FITC fluorescence is pH dependent becoming minimal as pH drops below about 6. Consequently, a label had to be found which could form a stable bond at pH below about 6 where the N-terminal amino acid could be preferentially labeled and ENP remained soluble. (It was speculated from some of the earlier experiments that labeling occurred inside the reactive loop of ENP. While it resulted in highly labeled ENP, it had significantly reduced the binding with LPS. See Exps. 5, 8, 9). The second challenge is to use a label whose fluorescence is relatively pH independent compared to FITC.

Experiments 0–8. These experiments used the FS label because it forms a more stable bond with amino groups and because it is recommended by Pan Vera Co. who sells the FS label for fluorescence polarization labeling. Variables included buffer composition, pH, and molar equivalents of FS, all of which were studied in an attempt to maximize the labeling of ENP. Experiments #2 and #7 produced reagents with a sensitivity of about 25 ng LPS. This represented a significant improvement over the FITC label. Fractionation of this labeled-ENP by reversed phase HPLC resulted in a reagent with sensitivity about 1 ng LPS. The label, however, is pH sensitive.

The results of the experiments are shown in Table 2 and FIGS. 1–4.

TABLE 2

| Expt # | Concn (mg/ml) | Volume (ml) | Buffer | pH | Reagent | Solvent | Concn (mg/ml) | Volume (ul) | Molar Equiv | Reaction Temp | Reaction Time | Isolation Buffer | % Labeling | |
|---|---|---|---|---|---|---|---|---|---|---|---|---|---|---|
| 1 | 2 | 1.25 | A | 4.5 | FITC | DMSO | 1 | 60 | 0.75 | RT | o/n | A | 0 | |
| 2 | 2 | 1.25 | B | 6.5 | FITC | DMSO | 1 | 60 | 0.75 | 4° C. | o/n | B | 1.4 | + |
| 3 | 2 | 1.25 | B | 6.5 | FITC | DMSO | 50 | 120 | 75 | RT | o/n | B | ** | |
| 4 | 2 | 1.25 | B | 6.5 | FITC | DMSO | 40 | 60 | 30 | RT | o/n | B | ** | |
| 5 | 2 | 1.25 | B | 6.5 | FITC | DMSO | 10 | 60 | 7.5 | RT | o/n | B | 36 | |
| 6 | 2 | 1.25 | A | 4.5 | FITC | DMSO | 10 | 60 | 7.5 | RT | o/n | A | 0 | |
| 7 | 2 | 1.25 | B | 6.5 | FITC | DMSO | 10 | 60 | 7.5 | RT | o/n | A | ? | |
| 8 | 2 | 1.25 | B | 6.5 | FITC | DMSO | 10 | 60 | 7.5 | RT | o/n | B" | 23 | |
| 9 | 2 | 1.25 | C | 6.5 | FITC | DMSO | 10 | 60 | 7.5 | RT | o/n | C | 64 | |
| 10 | 2 | 1.25 | C | 6.5 | FITC | DMSO | 1 | 60 | 0.75 | RT | o/n | C | 7 | |
| 11 | 2 | 1.25 | C | 6.5 | FITC | DMSO | 30 | 60 | 22.5 | RT | o/n | C | nd | |
| 12 | 2 | 1.25 | C | 6.5 | FITC | DMSO | 3 | 60 | 2.25 | RT | o/n | C | 14 | |
| 13 | 2 | 1.25 | D | 6 | FITC | DMSO | 10 | 60 | 7.5 | RT | o/n | D | 4 | |

| Expt # | Concn (mg/ml) | Volume (ml) | Buffer | pH | Reagent | Solvent | Concn (mmolar) | Volume (ul) | Molar Equiv | Reaction Temp (° C.) | Reaction Time (hr) | Isolation Buffer | % Labeling | |
|---|---|---|---|---|---|---|---|---|---|---|---|---|---|---|
| 0 | 1 | 1 | E | 7 | FS | DMSO | 10 | 50 | 6 | 37 | 1 | C | 61 | |
| 0 | 1 | 1 | E | 7 | FSX | DMSO | 10 | 50 | 6 | 37 | 1 | C | 60 | |
| 1 | 1 | 1 | F | 6 | FS | DMSO | 10 | 50 | 6 | 37 | 1 | D | 30 | |
| 2 | 1 | 1 | D | 6 | FS | DMSO | 10 | 50 | 6 | 37 | 1 | D | 5 | ++ |
| 3 | 1 | 1 | D | 6 | FS | DMSO | 10 | 50 | 6 | 37 | 1 | D | 5 | |
| 4 | 1 | 1 | D | 6 | FS | DMSO | 10 | 50 × 5^ | 30 | 37 | 2.5 | D | 35 | |
| 5 | 1 | 1 | D | 6 | FS | DMSO | 10 | 50 × 2^ | 12 | 37 | 1 | D | 17 | |
| 6 | 1 | 1 | G | 5 | FS | DMSO | 10 | 50 × 3^ | 18 | 37 | 1.5 | D | 13 | |
| 7 | 1 | 1 | H | 6 | FS | DMSO | 10 | 50 | 6 | 37 | 1 | D | 7 | +++ |
| 8 | 1 | 1 | J | 4.5 | FS | DMSO | 10 | 50 × 3^ | 18 | 37 | 1.5 | D | 12 | |
|   | 1 | 1 | F |   | FS | DMSO | 10 | 50 | 6 | 37 | 1 | D | ** | |
|   | 1 | 1 | H |   | FS | DMSO | 10 | 50 | 6 | 37 | 1 | D | ndnp | |
|   | 1 | 1 | H | 6 | BODIPY-FL SE | DMSO | 10 | 50 | 6 | 37 | 1 | H | | |
| 1 | 1 | 1 | H | 6 | BODIPY-FL SE | DMSO | 10 | 50 | 6 | 37 | 1 | H | | |
| 2 | 1 | 1 | H | 6 | BODIPY-TRX SE | DMSO | 10 | 50 | 6 | 37 | 1 | H | | |

** Protein precipitated
A 50 mM NaOAc, 0.9% NaCl, pH 4.5
B PBS, pH 6.5
B" PBS, pH 6.5, containing 10% DMSO
C 0.1M sodium phosphae, pH 6.5
D 0.1M sodium citrate, 6M urea, pH 6
E PanVera coupling buffer, phosphate
F 0.1M sodium citrate, pH 6
G 0.1M sodium citrate, 6M urea, pH 5
H 0.1M sodium citrate, 6M urea* (ultrapure), pH 6
J 0.25M NaOAc, 6M urea, pH 4.5
nd Not determined, needed to be passed through the PD10 column again to remove remaining FITC hydrolysis products and deemed not worthwhile
^ Added at 30 min intervals
ndnp Not determined, protein not pure
+---++++ Improvement in activity with respect to fluorescence polarization (FP)
Reaction solutions were separated on PD10 (G25M) columns (Pharmacia) in the isolation buffer (see above).

With the first preparation of FITC-R-ENP, low levels of labeling was obtained. The second attempt at labeling R-ENP gave FITC-R-ENP preps with 64% labeling. This material gave minimal detection by FP, but the activity was encouraging. The attempt to label N-ENP and R-ENP with FS from Pan Vera was only partially successful as only R-ENP could be so labeled.

The initial results indicated that the presence of urea in the labeling step appeared important, but not in the assay buffer. Sequential labeling steps did not result in increased labeling of ENP.

The optimum labeling procedure consists of using a 0.1M sodium citrate buffer with about 6M urea at pH about 6.0 with FS (about 6 molar equivalents) and add to a solution of recombinant ENP. The resultant mixture is purified by gel filtration and RPHPLC. The FS-ENP results in a reagent with approximately a 10 EU sensitivity.

Once the label is attached, the ENP may be purified by gel filtration, reversed phase HPLC, or affinity chromatography. The fractionation of labeled ENP from unlabeled ENP by HPLC worked well. The results in the FP assay (below) suggested that this additional step was necessary for improved sensitivity. However, the resultant product has a low pH which is good for ENP binding but compromises the intensity of the FS fluorophore. This has prompted the development of a pH insensitive fluorophore.

In an attempt to label a higher percentage of ENP molecules, sequential labeling (adding label in two or three steps) was tried. The resulting labeled tracer offered no enhanced sensitivity.

EXAMPLE 2
Fluorescent Polarization Experiments with ENP

The fluorescent polarization experiments were carried out according to the general procedures outlined above. The results are as follows.

Initial experiments with the FP equipment allowed detection of 500 ng LPS, and suggested that urea improved reaction and that DMSO diminished activity. Additional experimentation gave the indication that urea may be important in the labeling reaction of ENP, but may not be necessary in the assay buffer. Further experimentation showed that SDS, ZWITTERGET® Zwitterget, and urea are not necessary in the buffer. Pyrogen free water was found to be a superior assay medium, giving a test sensitivity of 25 ng.

There were successful attempts to measure LPS in aluminum rolling fluid emulsions. The emulsion was inoculated with bacteria. The sample was then tested against an uninoculated control using FP, which easily identified the test sample as contaminated. Metal cutting fluids, several of which were tested, exhibited some background fluorescence. Successful measurements of these types of fluids will involve use of an uninoculated control as a blank.

Other experiments were conducted in an effort to determine the specificity of the labeled ENP. It was found that unlabeled r-ENP reversed the binding reaction. In addition, antibody to ENP can be detected and is not reversed by unlabeled ENP or LPS. This suggest that perhaps there is a different site of attachment. However, the experiment confirmed the specificity.

The first attempt at using a FITC-labeled synthetic peptide fragment (a.a.'s 34–60 of SEQ ID NO:3 or a.a.'s 30–56 of SEQ ID NO:1) did not bind LPS. The unlabeled peptide did bind LPS and reversed the binding of fluorescently labeled ENP to LPS. A second lot of synthetic peptide fragment labeled, however, with FS instead of FITC did bind LPS in the FP assay.

Since there is a relationship between the percent of ENP molecules that are labeled and the number of molecules of endotoxin that are detectable (sensitivity), it was confirmed that under the current conditions for labeling ENP, an optimum concentration of ENP was found and, generally, lower concentrations of labeled ENP detect lower levels of endotoxin.

The effect of pH on the intensity and binding of ENP was also examined. It was found that with FS label, intensity increased as pH was raised to 8.9 but binding of LPS was absent. Binding was detectable at pH 3.9, which suggests using a pH insensitive label, e.g. bodipy-TR.

In order to optimize the sensitivity, one may vary the buffer composition and buffer pH.

The effects of other LPS binding molecules present in biological fluids on the reaction kinetics and sensitivity may be taken into account when carrying out an assay on such a fluid. Such LPS binding molecules include polymyxin B, heparin, albumin, lysozyme, and antibodies.

EXAMPLE 3
A Comparison of Endotoxin Concentration in Metal Working Fluids and in Air Samples Using Different Methods of Assay Oregon Green-labeled ENP was prepared according to Example 1, except that Oregon Green was substituted for FS. The results of fluroescent polarization assays ("EndoFluor") using Oregon Green-labeled ENP on various samples is shown in Table 3.

TABLE 3

| SAMPLE | GelClot | Turbimetric | EndoFluor |
|---|---|---|---|
| MWF #1 | 12,000–50,000 | 50,000–175,000 | 55,686 |
| Air Sample #1 | 17–68 | 95 | 995 |
| MWF #2 | 250–1,000 | 3,030 | 37,054 |
| Air Sample #2 | 17–35 | 59 | 1,650 |
| MWF #3 | 12,000–50,000 | 38,000–100,000 | 87,722 |
| Air Sample #3 | 4–16 | 13 | 1,770 |

MWF = Metal Working Fluid - Endotoxin concentration is expressed as EU/ml
Air Samples were taken from the area surrounding the respective MWF using a liquid impinger - Endotoxin concentration is expressed as EU/cubic meter of air.

Although the foregoing invention has been described in some detail by way of illustration and example, for purposes of clarity and understanding, it will be obvious that certain changes and modifications may be practiced within the scope of the invention, as limited only by the scope of the appended claims. All patents, published patent applications and U.S. Patent Applications disclosed herein are incorporated herein in their entirety.

---

What is claimed is:

1. A method of preparing fluorescently labeled Endotoxin Neutralizing Protein, comprising combining in an aqueous citrate buffer solution Endotoxin Neutralizing Protein, urea, and fluorescein N-hydroxysuccinimide ester, and isolating the fluorescently labeled Endotoxin Neutralizing Protein from the solution.

2. The method of claim 1, wherein the Endotoxin Neutralizing Protein has the sequence set forth in SEQ ID NO:3.

3. A method of detecting endotoxin in a liquid sample suspected of containing endotoxin, comprising admixing said liquid sample with fluorescently labeled Endotoxin Neutralizing Protein (SEQ ID NO:3) for a time sufficient to form a complex between the labeled Endotoxin Neutralizing Protein (SEQ ID NO:3) and the endotoxin, and performing a fluorescence polarization experiment on said sample to obtain a fluorescence polarization value, wherein a change in the fluorescence polarization value after formation of the complex indicates the presence of endotoxin, wherein the fluorescence polarization experiment comprises:

(a) inserting a control container containing buffer or water into a fluorescence polarization analyzer;

(b) adding a predetermined amount of a standard solution of the fluorescently labeled Endotoxin Neutralizing Protein (SEQ ID NO:3) to the control container to obtain a solution, and measuring the fluorescence polarization to give a baseline measure of fluorescence polarization;

(c) adding to the solution obtained in (b) a series of known concentrations of lipopolysaccharide to obtain a mixture, and recording any change in fluorescence polarization; and (d) adding to the solution obtained in (b) or to the mixture obtained in (c) the complex comprising fluorescently labeled Endotoxin Neutralizing Protein (SEQ ID NO:3) and endotoxin, and recording any change in fluorescence polarization.

4. A method of quantifying endotoxin in a liquid sample suspected of containing endotoxin, comprising admixing said liquid sample with fluorescently labeled Endotoxin Neutralizing Protein (SEQ ID NO:3) for a time sufficient to form a complex between the labeled Endotoxin Neutralizing Protein (SEQ ID NO:3) and the endotoxin, and performing a fluorescence polarization experiment on said sample, wherein any relative change in fluorescence polarization after the complex is formed is a measure of the quantity of endotoxin in said sample, wherein said fluorescence polarization experiment comprises:

(a) inserting a control container containing buffer or water into a fluorescence polarization analyzer;

(b) adding a predetermined amount of a standard solution comprising Endotoxin Neutralizing Protein (SEQ ID NO:3) to the control container to obtain a solution, and measuring the fluorescence polarization to give a baseline measure of fluorescence polarization;

(c) adding to the solution obtained in (b) a series of known concentrations of lipopolysaccharide to obtain a mixture, recording any change in fluorescence polarization, and plotting the changes to give a standard curve; and (d) adding to the solution obtained in (b) or to the mixture obtained in (c) the complex comprising fluorescently labeled Endotoxin Neutralizing Protein (SEQ ID NO:3) and endotoxin, and recording any change in fluorescence polarization.

5. The method of claim 3 or 4, wherein said sample is an oil-in-water emulsion used as a coolant ofr metal cutting, aluminum or steel rolling, or metal forming; a rust preventive; a metal cleaner; a metal heat treating fluid; a paint; an adhesive; a food product; a food handling surface; waste water; cooling tower water; a personal care product; a pharmaceutical product; or a medical diagnostic product.

6. The method of claim 3 or 4, wherein said sample is blood, urine, CSF, or a lavage.

7. The method of claim 3 or 4, wherein said standard solution comprises fluorescently labeled Endotoxin Neutralizing Protein (SEQ ID NO:3 ) and pyrogen free water.

8. The method of claim 3 or 4, wherein said complex-containing solution obtained in (d) comprises the sample suspected of containing endotoxin, fluorescently labeled Endotoxin Neutralizing Protein (SEQ ID NO:3), and pyrogen free water.

9. A method of detecting endotoxin in a liquid sample suspected of containing endotoxin, comprising:

(a) admixing a defined concentration of Endotoxin Neutralizing Protein with a defined concentration of fluorescently labeled lipopolysaccharide for a time sufficient to form a complex between the labeled lipopolysaccharide and the Endotoxin Neutralizing Protein;

(b) performing a fluorescence polarization experiment on the admixture obtained according to (a) to give a first fluorescence polarization value;

(c) admixing a sample suspected of containing endotoxin with the admixture obtained in (a); and (d) performing a fluorescence polarization experiment on the admixture obtained in (c) to give a second fluorescence polarization value;

wherein a change in the second fluorescence polarization value with respect to the first fluorescence polarization value indicates the presence of endotoxin.

10. A method of quantifying endotoxin in a liquid sample suspected of containing endotoxin, comprising:
    (a) admixing a defined concentration of Endotoxin Neutralizing Protein with a defined concentration of fluorescently labeled lipopolysaccharide for a time sufficient to form a complex between the labeled lipopolysaccharide and the Endotoxin Neutralizing Protein;
    (b) performing a fluorescence polarization experiment on the admixture obtained according to (a) to give a first fluorescence polarization value;
    (c) admixing a sample suspected of containing endotoxin to the admixture obtained in (a); and
    (d) performing a fluorescence polarization experiment on the admixture obtained in (c) to give a second fluorescence polarization value;

wherein the relative change in the second fluorescence polarization value with respect to the first fluorescence polarization value is a measure of the quantity of endotoxin in said sample.

11. The method of claim 9 or 10, wherein said sample is an oil-in-water emulsion used as a coolant for metal cutting, aluminum or steel rolling, or metal forming; a rust preventive; a metal cleaner; a metal heat treating fluid; a paint; an adhesive; a food product; a food handling surface; waste water; cooling tower water; a personal care product; a pharmaceutical product; or a medical diagnostic product.

12. The method of claim 9 or 10, wherein said sample is blood, urine, CSF, or a lavage.

13. The method of claim 10, wherein said admixing in (c) is achieved by passing an air sample suspected of containing endotoxin through the admixture obtained in step (a).

* * * * *